(12) United States Patent
Bani-Hashemi (10) Patent No.: US 7,249,854 B2
(45) Date of Patent: Jul. 31, 2007

(54) VIRTUAL DIGITAL SHAPE PROJECTOR

(75) Inventor: Ali Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 268 days.

(21) Appl. No.: 11/123,747

(22) Filed: May 4, 2005

(65) Prior Publication Data

US 2006/0250586 A1    Nov. 9, 2006

(51) Int. Cl.
   *G03B 21/26*    (2006.01)
(52) U.S. Cl. .......................................... 353/94; 378/206
(58) Field of Classification Search .................. 353/94; 378/20, 206
   See application file for complete search history.

(56) References Cited

U.S. PATENT DOCUMENTS

| 6,088,106 A | 7/2000 | Röckseisen |
| 6,364,506 B1 * | 4/2002 | Gallo ......................... 362/245 |
| 2002/0012420 A1 * | 1/2002 | Bani-Hashemi et al. ...... 378/63 |

* cited by examiner

*Primary Examiner*—D. Rutledge (57) ABSTRACT

A projection system for projecting a shape onto a scene (e.g., the surface of an object, the body of a patient, or the like) so that the shape appears to be projected via a light beam emanating from a desired source location includes two or more projection assemblies for projecting planes of light which intersect the scene to form light stripes on the scene. The intersection of the light stripes defines a point of light projected onto the scene so that the point of light appears to emanate from the source location. The first and second projection assemblies rotate about first and second axes which extend through the source location for controlling the position of the point of light on the scene.

21 Claims, 7 Drawing Sheets

VIRTUAL DIGITAL SHAPE PROJECTOR

BACKGROUND OF THE INVENTION

The present invention relates generally to apparatus and method for projecting a shape onto a scene, and more particularly to a system and method for projecting a shape onto a scene so that the shape appears to be projected via a light beam emanating from a desired source location.

There are several applications in industry that may benefit from projecting a shape into a scene (e.g., onto the surface of an object). In these applications, the intention is typically to guide a user during the performance of a task, for example, to guide a user during mechanical repair of complex systems, or to guide a user during patient set-up for radiation oncology.

In radiation oncology, a light field is typically used to represent the geometry and profile of high-energy beams that treat patients. A mirror angled at forty five degrees (45°) is positioned on a central axis of the radiation beam to bend a beam of light as if it originated from the radiation source. This method of precision alignment may achieve congruence of the light field with the radiation field. However, the method has several limitations. First, the physical characteristics of visible light are different from those of high-energy gamma rays, X-rays, or the like. For example, X-rays penetrate the beam limiting devices (e.g., jaws or maximum contaminate level (MLC) leaves), which may result in the penumbra phenomenon, where a penumbra extends the effective field beyond what is illuminated by the light field. Also, it is not possible to illuminate the scene beyond the field opening. Further, in certain situations, it may be desirable for the X-ray beam to pass through a 2-dimensional detector for entrance dosimetry. To benefit from a visible light field, such as for visual alignment, it would be necessary to move the two-dimensional detector out of the beam path, thereby adding to the design complexity of the radiation treatment device.

Consequently, it would be advantageous to provide a projection system for projecting a shape onto a scene (e.g., the surface of an object) so that the shape appears to be projected via a light beam emanating from a desired source location which may not be accessible, such as, for example, the radiation source of a radiation treatment device used in radiation oncology.

SUMMARY OF THE INVENTION

The present invention is directed to a virtual digital projection system for projecting a shape onto a scene (e.g., the surface of an object) so that the shape appears to be projected via a light beam emanating from a desired source location which may not be accessible. In exemplary embodiments, the projection system includes two or more projection assemblies which project planes of light that intersect the scene to form light stripes on the scene. The intersection of the light stripes defines one or more points of light projected onto the scene so that the point(s) of light appear to emanate from the source location. The projection assemblies rotate about axes which extend through the source location for controlling the position of the point(s) of light on the scene. The projection system is particularly suitable for use in radiation oncology for projecting a pattern or target onto the body of a patient during radiation treatment so that the pattern appears to emanate from the radiation source.

In one specific embodiment, the present invention provides a system for projecting a shape onto a scene so that the shape appears to emanate from a source location. The system comprises a first projection assembly for projecting a first plane of light so that the first plane of light intersects the scene to form a first light stripe on the scene and a second projection assembly for projecting a second plane of light so that the second plane of light intersects the scene to form a second light stripe on the scene. The first and second projection assemblies are oriented so that the first light stripe intersects the second light stripe for defining a point of light projected onto the scene, wherein the point of light appears to emanate from the source location. The first projection assembly rotates about a first axis extending through the source location, while the second projection assembly rotates about a second axis extending through the source location allowing the position of the point of light on the scene to be controlled. In this manner, the shape may be traced onto the scene by projecting, in turn, a plurality of light points onto the scene corresponding to points in the shape to be projected.

In a second specific embodiment, the present invention provides a method for projecting a shape onto a scene so that the shape appears to emanate from a source location. The method comprises the steps of projecting a first plane of light from a first projection assembly so that the first plane of light intersects the scene to form a first light stripe on the scene; projecting a second plane of light from a second projection assembly so that the second plane of light intersects the scene to form a second light stripe on the scene, the first light stripe intersecting the second light stripe for defining a point of light projected onto the scene so that the point of light appears to emanate from the source location; and rotating at least one of the first projection assembly about a first axis extending through the source location and the second projection assembly about a second axis extending through the source location for controlling the position of the point of light on the scene. The method may be repeated for different locations on the object, for tracing the shape onto the scene by projecting, in turn, a plurality of light points onto the scene corresponding to points in the shape to be projected.

It is to be understood that both the foregoing general description and the following detailed description are exemplary and explanatory only and are not necessarily restrictive of the invention claimed. The accompanying drawings, which are incorporated in and constitute a part of the specification, illustrate embodiments of the invention and together with the general description, serve to explain the principles of the invention.

DETAILED DESCRIPTION OF SPECIFIC EMBODIMENTS

Reference will now be made in detail to the presently preferred embodiments of the invention, examples of which are illustrated in the accompanying drawings.

Referring generally to FIGS. 1 through 4, an exemplary system 100 is described for projecting a shape 102 onto a scene 104 such as the surface of an object or article of manufacture, the body of a person such as a patient being treated using radiation therapy, or the like, so that the shape 102 appears to be projected from a light beam emanating from a source location S 106. In exemplary embodiments, the system 100 includes two or more projection assemblies which project planes of light that intersect the scene 104 to form light stripes on the scene 104. The intersection of the light stripes defines one or more points of light projected onto the scene so that the point(s) of light appear to emanate from the source location, point S 106. The projection assemblies rotate about axes which extend through the source location, point S 106, for controlling the position of the point(s) of light on the scene. For example, in the specific embodiment shown in FIG. 1, the system 100 includes a first projection assembly 108 for projecting a first plane of light 110 so that the first plane of light 110 intersects the scene 104 to form a first light stripe 112 on the scene 104 and a second projection assembly 114 for projecting a second plane of light 116 so that the second plane of light 116 intersects the scene 104 to form a second light stripe 118 on the scene 104. The first projection assembly 108 and the second projection assembly 114 are oriented so that the first light stripe 112 intersects the second light stripe 118 for defining a point of light at point O 120 projected onto the scene 104. In this manner, the point of light O 120 may be made to appear to emanate from the source location 106.

Figure 1:
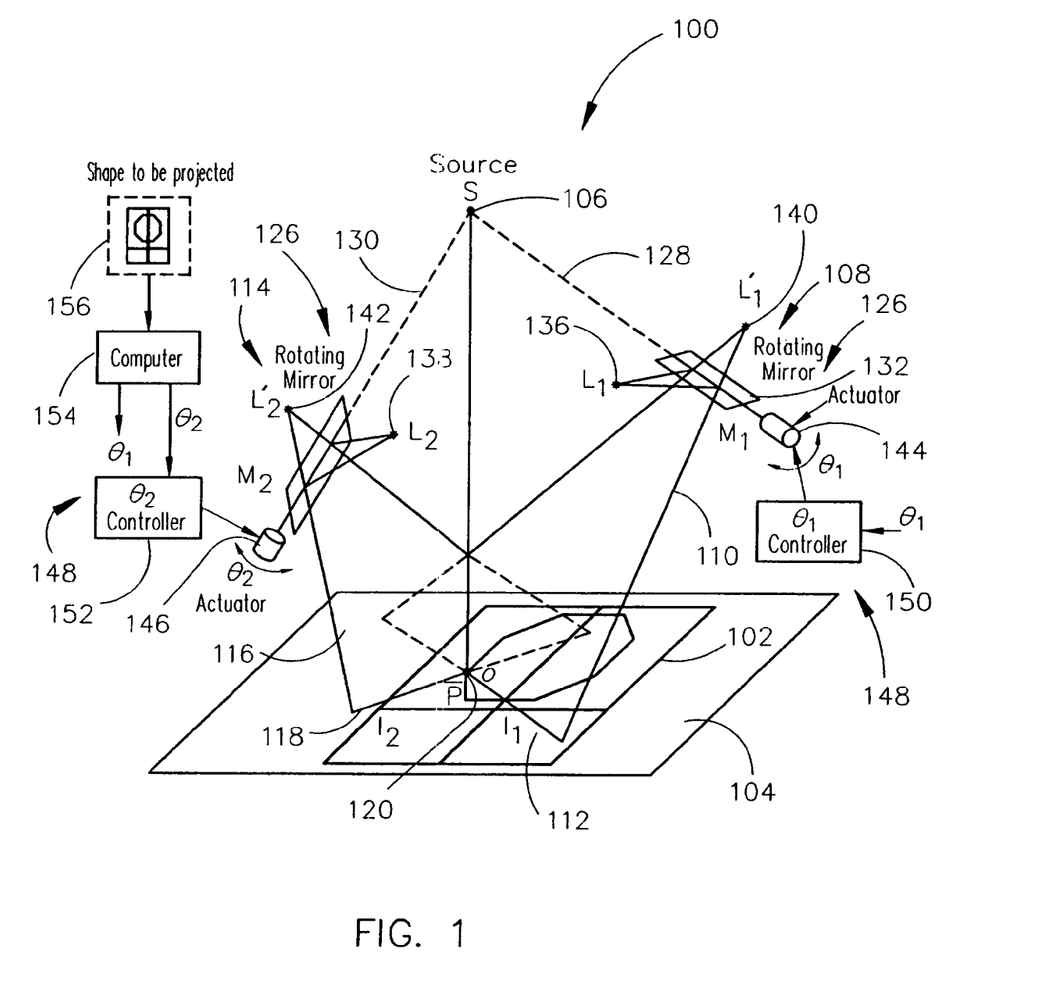
FIG. 1 is a block diagram illustrating a system for projecting a shape onto a scene so that the shape appears to emanate from a source location in accordance with an exemplary embodiment of the present invention.
Figure 2:
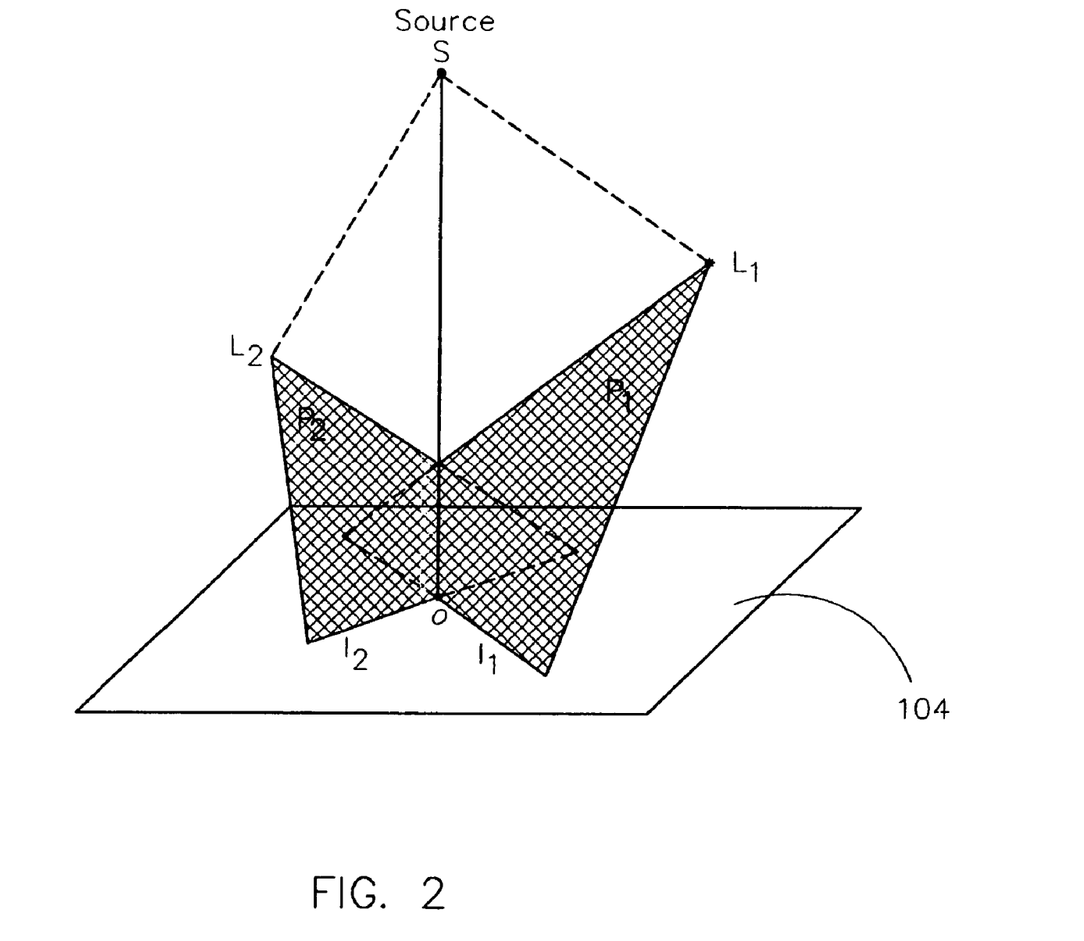
FIG. 2 is a diagram illustrating the geometry used by the system shown in FIG. 1 for creating a virtual beam.
Figure 3:
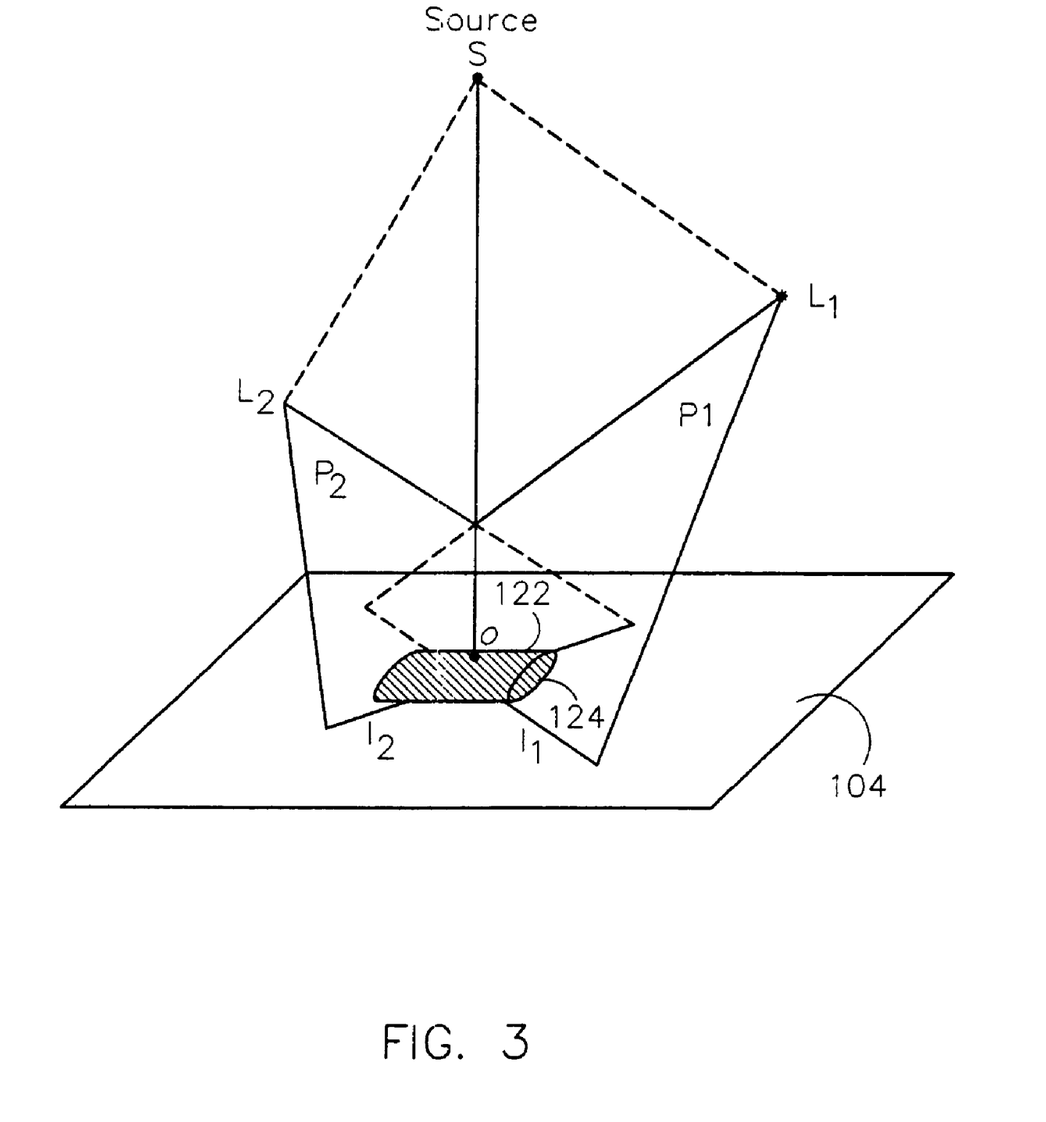
FIG. 3 is a diagram illustrating intersection of the a virtual beam created using the geometry shown in FIG. 2 with the surface of an object.

FIGS. 2 and 3 illustrate the geometry used by the system 100 shown in FIG. 1 for projection a point of light at point O as if point O were projected via a virtual beam emanating from the source location. Point S is the source location from which point O appears to be projected. Light sources $L_1$ and $L_2$ each project a sheet or plane of light onto the scene 104. Planes $P_1$ and $P_2$ represent the planes of light associated with light sources $L_1$ and $L_2$, respectively. The intersection of planes $P_1$ and $P_2$ with the scene result in lines or stripes of light $l_1$ and $l_2$ being projected onto the scene 104, which intersect at point O. Planes $P_1$ and $P_2$ pass through point S, the virtual source. Thus, the line SO represents an imaginary beam, or virtual beam, emanating from point S and projected onto the scene 104 at point O such that point O is an illuminated point on the scene 104 lying along the virtual beam from source S to point O.

In accordance with the present invention, plane $P_1$ may be rotated about point $L_1$, with line $SL_1$ defining an axis of rotation about which the plane of light rotates. Plane $P_1$ includes point S. Likewise, plane $P_2$ may be rotated about point $L_2$, with line $SL_2$ defining a second rotation axis about which the plane of light rotates. Plane $P_2$ thus also includes point S. In this manner, point O may be moved over the scene, but will be illuminated as if a light beam originated from point S. The angle of rotations of planes $P_1$ and $P_2$ may be adjusted such that point O may be moveable to scan the scene.

As shown in FIG. 3, the intersection of planes $P_1$ and $P_2$ with the surface 122 three-dimensional (3D) object 124 introduced into the scene 104 results in light stripes light $l_1$ and $l_2$ being shaped to match the surface 122 (e.g., curved, angled, or the like) along an axis parallel to line SO. Point O marks an intersection of light stripes $l_1$ and $l_2$ on the surface 122 of the object 124. In this manner, point O is projected onto the surface 122 of the object 124 so that the characteristics of point O make point O appear to be projected by a beam emanating from point S.

Figure 4:
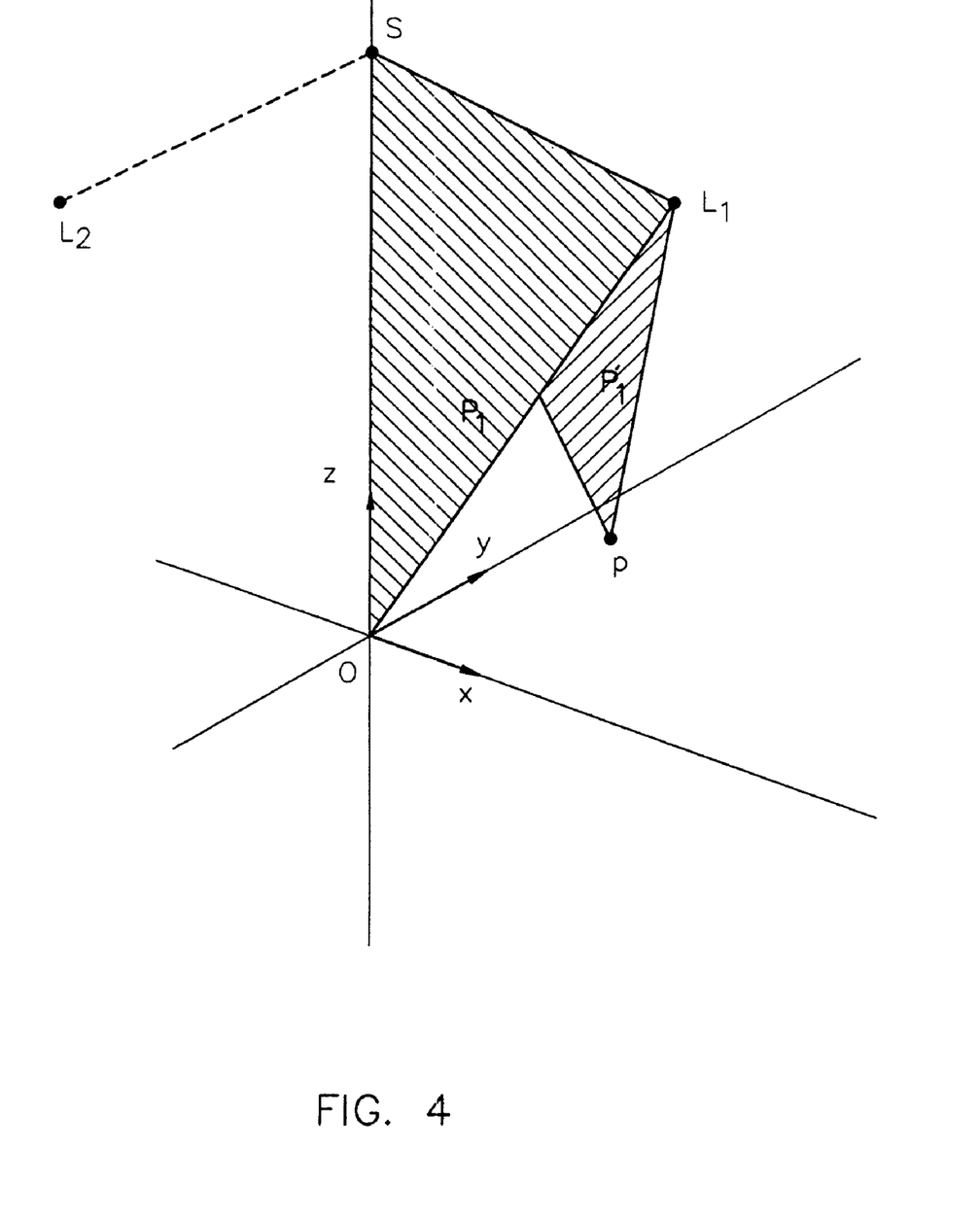
FIG. 4 is a diagram illustrating the projection of a shape onto a scene by repeatedly projecting the virtual beam onto different points in the scene (e.g., in a raster fashion, or the like)

Referring now to FIG. 4, the position of the projected point of light, point O in FIGS. 1, 2 and 3, may be adjusted by rotating the planes of light about rotation axes $L_1S$ and $L_2S$. FIG. 4 illustrates a world coordinate frame (x, y, z) that may be utilized for describing the projection of point O at various points within the scene in an exemplary embodiment of 104 (FIG. 1) the present invention. This world coordinate system may be adapted to the particular system application. For example, in radiation oncology application, the world coordinate system may be an IEC (International Engineering Consortium) coordinate frame, where the radiation source S lies along the z axis.

A shape or pattern to be projected may be digitally represented by a set of points on a plane. For example, in radiation oncology applications, shapes may be represented as set of points on an isocentric plane. To project a shape digitally into a scene, such as the scene 104 shown in FIG. 1, an intersection point $\bar{p}$ traverses all points that form the digital shape in some pattern (e.g., tracing the shape, in a raster pattern, or the like). The point $\bar{p}$ is illuminated by the two planes of light passing through the point S.

In FIG. 4, point $\bar{p}$ is the desired illumination point, which is created by the intersection of the light stripes of planes of light $P_1$ and $P_2$. Plane $P_2$ is not shown in FIG. 4 for clarity of illustration but is illustrated in FIGS. 1, 2, and 3. Point $\bar{p}$ is described in the world coordinate frame (x, y, z). Accordingly, the intersection of plane $P_1$ and plane $P_2$ with no rotation about rotation axes $L_1S$ and $L_2S$ causes point $\bar{p}$ to be illuminated at the origin, point O, of the world coordinate frame (x, y, z). Point $\bar{p}$ is projected at other locations by rotating plane $P_1$ and plane $P_2$ with no rotation about rotation axes $L_1S$ and $L_2S$, respectively. For example, as shown in FIG. 4, plane $P_1'$ illustrates the rotation of plane $P_1$ about line $SL_1$. Similarly, plane $P_2'$, although not illustrated, would be the rotation of plane $P_2$ about line $SL_2$. The intersection of the light stripes of planes $P_1'$ and $P_2'$ projects or illuminates point $\bar{p}$ at a location other than the origin, point O. The angle of rotation of planes $P_1'$ and $P_2'$ about $L_1S$ and $L_2S$ from planes $P_1$ and $P_2$ may be calculated from:

$$\theta_1 = \sin^{-1}(|\hat{N}_1 \times \hat{N}_1'|) \qquad \text{EQ. 1}$$

and $$\theta_2 = \sin^{-1}(|\hat{N}_2 \times \hat{N}_2'|); \qquad \text{EQ. 2}$$

where $\theta_1$ is the angle of rotation by which plane $P_1$ rotates about the rotation axis $SL_1$ in order to illuminate or project point $\bar{p}$. $\theta_2$ is the angle of rotation by which plane $P_2$ rotates about the rotation axis $SL_2$ in order to illuminate or project point $\bar{p}$, $\hat{N}_1$ is the unit normal to plane $P_1$, and is calculated from:

$$\hat{N}_1 = \frac{\overline{L_1} \times \overline{S}}{|\overline{L_1}||\overline{S}|};\qquad \text{EQ. 3}$$

$\hat{N}_1{}'$ is the unit normal to plane $P_1{}'$, and is calculated from:

$$\hat{N}_1' = \frac{(\overline{L_1} - \overline{p}) \times (\overline{S} - \overline{p})}{|\overline{L_1} - \overline{p}||\overline{S} - \overline{p}|};\qquad \text{EQ. 4}$$

$\hat{N}_2$ is the unit normal to plane $P_2$, and is calculated from:

$$\hat{N}_2 = \frac{\overline{L_2} \times \overline{S}}{|\overline{L_2}||\overline{S}|};\qquad \text{EQ. 5}$$

and $\hat{N}_2{}'$ is the unit normal to plane $P_2{}'$, and is calculated from:

$$\hat{N}_2' = \frac{(\overline{L_2} - \overline{p}) \times (\overline{S} - \overline{p})}{|\overline{L_2} - \overline{p}||\overline{S} - \overline{p}|}.\qquad \text{EQ. 6}$$

Accordingly, as shown in FIG. 1, the system 100 of the present invention may digitally project a shape 102 by rotating intersecting planes of light 128 & 130 about rotation axes passing through the source location, point S 106. As shown in FIG. 1, the system 100 includes an actuator assembly 126 that rotates the first projection assembly 108 about a first axis 128 extending through the source location, point S 106, and the second projection assembly 114 about a second axis 130 also extending through the source location, point S 106. In this manner, the position of the point of light (i.e., the point $\overline{p}$) 120 on the scene 104 may be controlled allowing the shape 102 to be traced onto scene 104 by projecting, in turn, the point of light at a plurality of locations within the scene 104.

In the exemplary embodiment illustrated, the first projection assembly 108 includes a first mirror $M_1$ 132 and the second projection assembly 114 includes a second mirror $M_2$ 134. A first light source $L_1$ 136 projects the first plane of light 110 onto the first mirror $M_1$ 132 for reflection by the first mirror $M_1$ 132 onto the scene 104. Likewise, a second light source $L_2$ 138 projects the second plane of light 116 onto the second mirror $M_2$ 138 for reflection by the second mirror $M_2$ so that the light stripes $l_1$ 112 and $l_2$ 118 formed by the first plane of light 110 and the second plane of light 116 intersect to form the point of light (e.g., point $\overline{p}$). Thus, the lights sources $L_1$ 136 and $L_2$ 138 appear to located at points $L_1{}'$ 140 and $L_2{}'$ 142. A first actuator 144 is coupled to the first mirror $M_1$ 132 and rotates the first mirror $M_1$ 132 about the first axis 128 though the angle $\theta_1$ for reflecting the first plane of light 110 for projecting the first plane of light 110 so that the first light stripe $l_1$ 112 is positioned at desired location on the scene 104. Likewise, a second actuator 146 is coupled to the second mirror $M_2$ 134 and rotates the second mirror $M_2$ 134 about the second axis 130 though the angle $\theta_2$ for reflecting the second plane of light 116 to project the second plane of light 116 onto the scene 104 so that the second light stripe $l_2$ 118 is positioned at a desired location on the scene 104, wherein the second light stripe $l_2$ 112 intersects the first light stripe $l_1$ 112 at the desired point, point $\overline{p}$ 120. Alternatively, the first light source $L_1$ 136 and the second light source $L_2$ 138 may project the first and second planes of light 110 and 116 directly onto the scene 104. In this embodiment, mirrors $M_1$ 132 and $M_2$ 134 are not required. Instead, the light sources $L_1$ 136 and $L_2$ 138 are positioned at points $L_1{}'$ 140 and $L_2{}'$ 142 and are themselves rotated through angles $\theta_1$ and $\theta_2$ about axes extending through the source location, point S 106, by the actuators 144 and 146 of the actuator assembly 126.

Any suitable actuator may be utilized for rotating the mirrors $M_1$ 132 and $M_2$ 134, or alternatively, light sources $L_1$ 136 and $L_2$ 138 in embodiments where the light sources $L_1$ 136 and $L_2$ 138 project the first and second planes of light 110 and 116 directly onto the scene 104. For example, in one embodiment, the actuators 144 and 146 may comprise scanning type galvanometers. Galvanometers comprise very high speed, current sensitive, limited rotation, bipolar devices, wherein the amount of rotation (within the rotational limits of the galvanometer) is determined by the amount of current applied. The direction of the limited rotation of the galvanometer is controlled by the polarity of the current applied.

The system 100 shown in FIG. 1 further includes a controller assembly 148 for controlling rotation of the first projection assembly 108 and the second projection assembly 114 and controlling the position of the point of light, point $\overline{p}$ 120, projected onto the scene 104. In the specific embodiment illustrated, the controller assembly 148 includes a first controller 150 for controlling the angle of rotation $\theta_1$ of the first mirror $M_1$ 132 by the first actuator 144 and a second controller 152 for controlling the angle of rotation $\theta_2$ of the second mirror $M_2$ 134 by the second actuator 146. The first and second angles of rotation $\theta_1$ and $\theta_2$ are provided to the respective controllers 150 and 152 by a computer 154, which generates the first and second angles of rotation $\theta_1$ and $\theta_2$ from the position or coordinates of the point $\overline{p}$ in the shape 156 to be projected onto the scene 104 in the world coordinate frame (x, y, z). The conversion of the coordinates of point $\overline{p}$ to the angles of rotation $\theta_1$ and $\theta_2$ may be accomplished using EQ. 1 and EQ. 2, respectively, as discussed in the description of FIG. 3.

Figure 5:
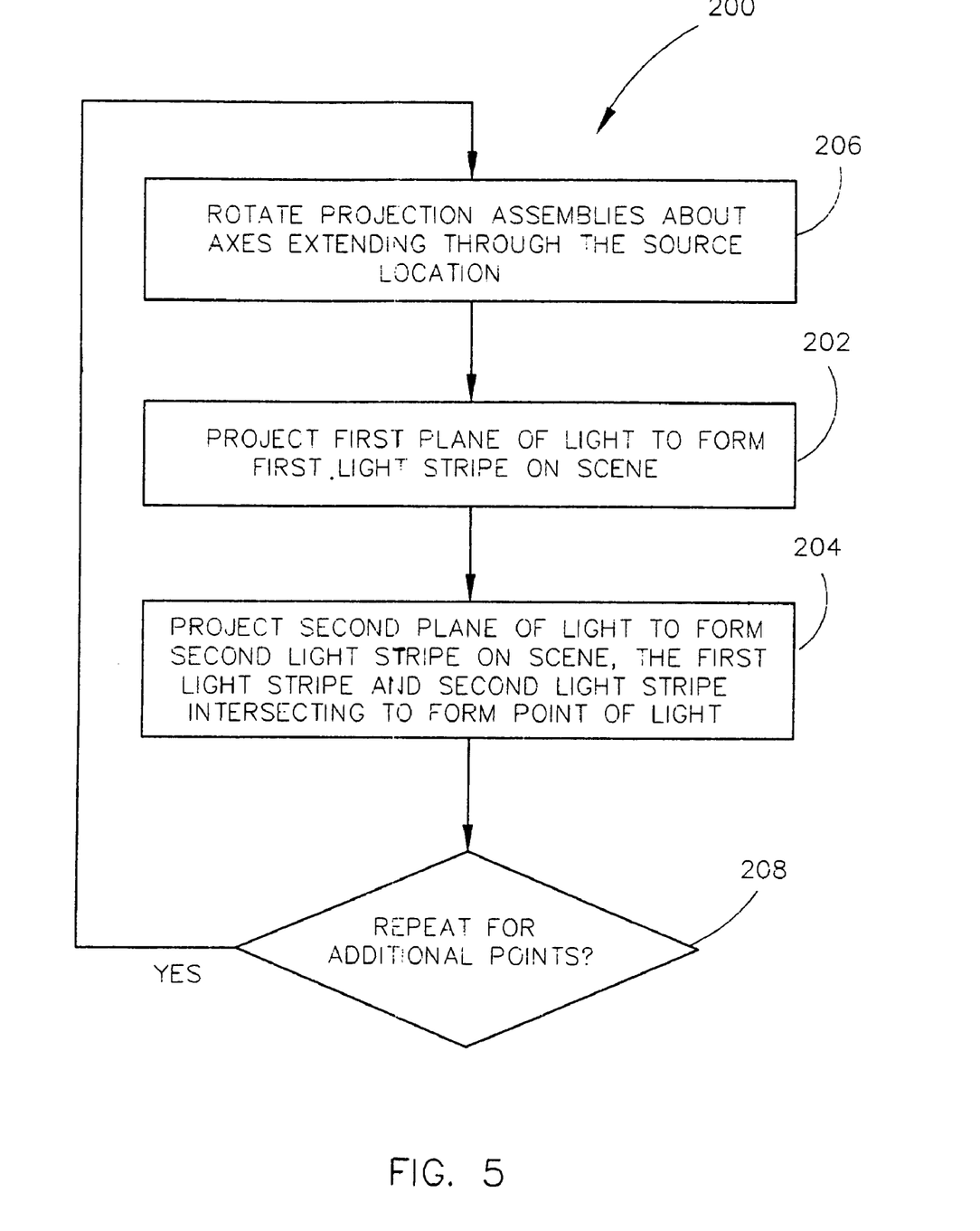
FIG. 5 is a flow diagram illustrating an exemplary method, suitable for use by the system shown in FIG. 1, for projecting a shape onto a scene so that the shape appears to emanate from a source location.

FIG. 5 illustrates an exemplary method 200, suitable for use by the system 100 shown in FIG. 1, for projecting a shape 102 onto a scene 104 so that the shape 102 appears to emanate from a source location, point S 106. The shape to be projected may be represented digitally by a set of points $\overline{p}$ in a world coordinate frame (x, y, z) and stored in the memory of a computer. Each point $\overline{p}$ may be converted to a corresponding angle of rotation $\theta_1$ and $\theta_2$ by the computer and provided to controllers for controlling projection of the point $\overline{p}$. As shown in FIG. 5, a first plane of light is projected from a first projection assembly so that the first plane of light intersects the scene to form a first light stripe on the scene at step 202. Likewise, a second plane of light is projected from a second projection assembly so that the second plane of light intersects the scene to form a second light stripe on the scene, at step 204. The first light stripe intersects the second light stripe for defining a point of light projected onto the scene so that the point of light appears to emanate from the source location. The first projection assembly may be rotated about a first axis extending through the source location and/or the second projection assembly may be rotated about a second axis extending through the source location for controlling the position of the point of light on the scene, at step 206. In exemplary embodiments, the projection assemblies (e.g., mirrors) may be moved to the desired angles of rotation $\theta_1$ and $\theta_2$, and the light sources then turned on to illuminate point $\overline{p}$ on the scene. The light sources may then be turned off and the mirrors moved to illuminate a new point. The method 200 may be repeated, at step 208, for all points in the set of points $\overline{p}$, and may restart at an initial point in the set in a continuous loop for scanning or tracing the shape onto the scene. The method 200 is repeated until the shape is no longer to be projected.

In exemplary embodiments, the method 200 may be implemented as computer-executable instructions (e.g., software, firmware, or the like) and may be stored in a computer-readable medium and executed by a computer, the control system of a radiation treatment device such as a linear accelerator (LINAC), or the like. It is understood that the specific order or hierarchies of steps in the methods disclosed are examples of exemplary approaches. Based upon design preferences, it is understood that the specific order or hierarchy of steps in the method can be rearranged while remaining within the scope of the present invention. The attached method claims present elements of the various steps in a sample order, and are not meant to be limited to the specific order or hierarchy presented.

Figure 6:
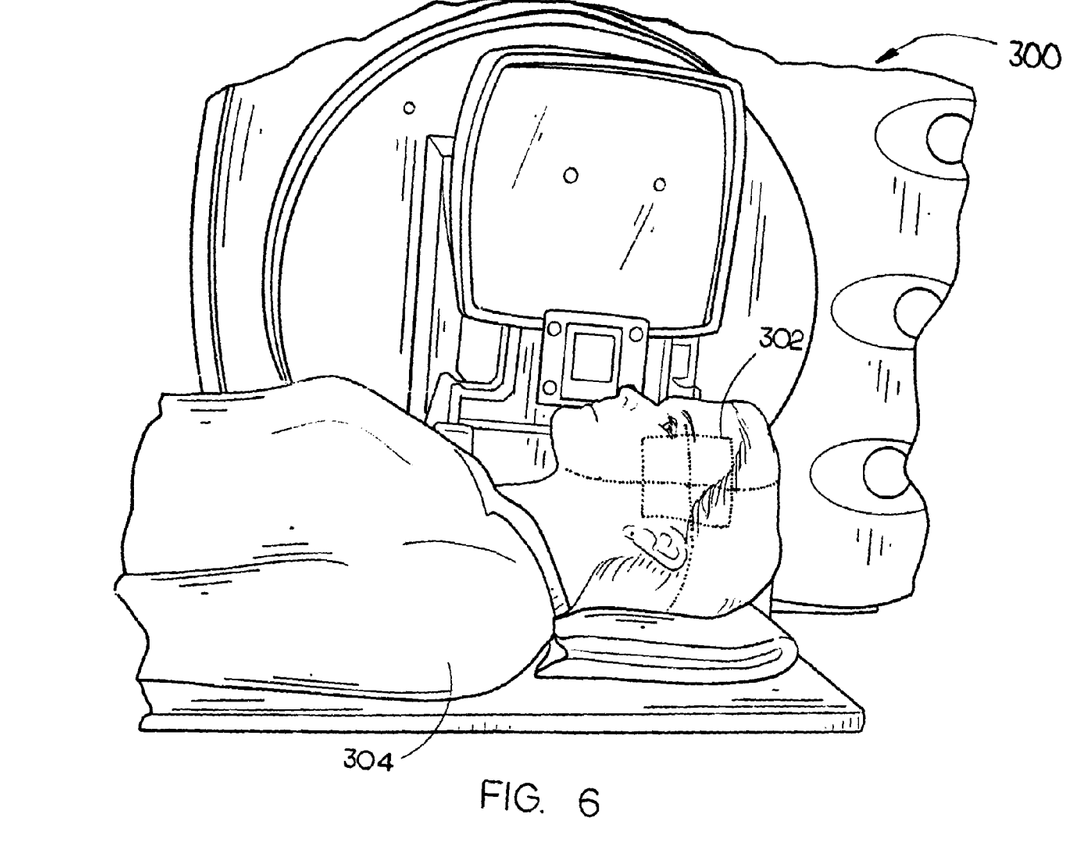
FIGS. 6 and 7 are isometric views illustrating the projection of virtual digital shapes onto patients during radiation treatment.
Figure 7:
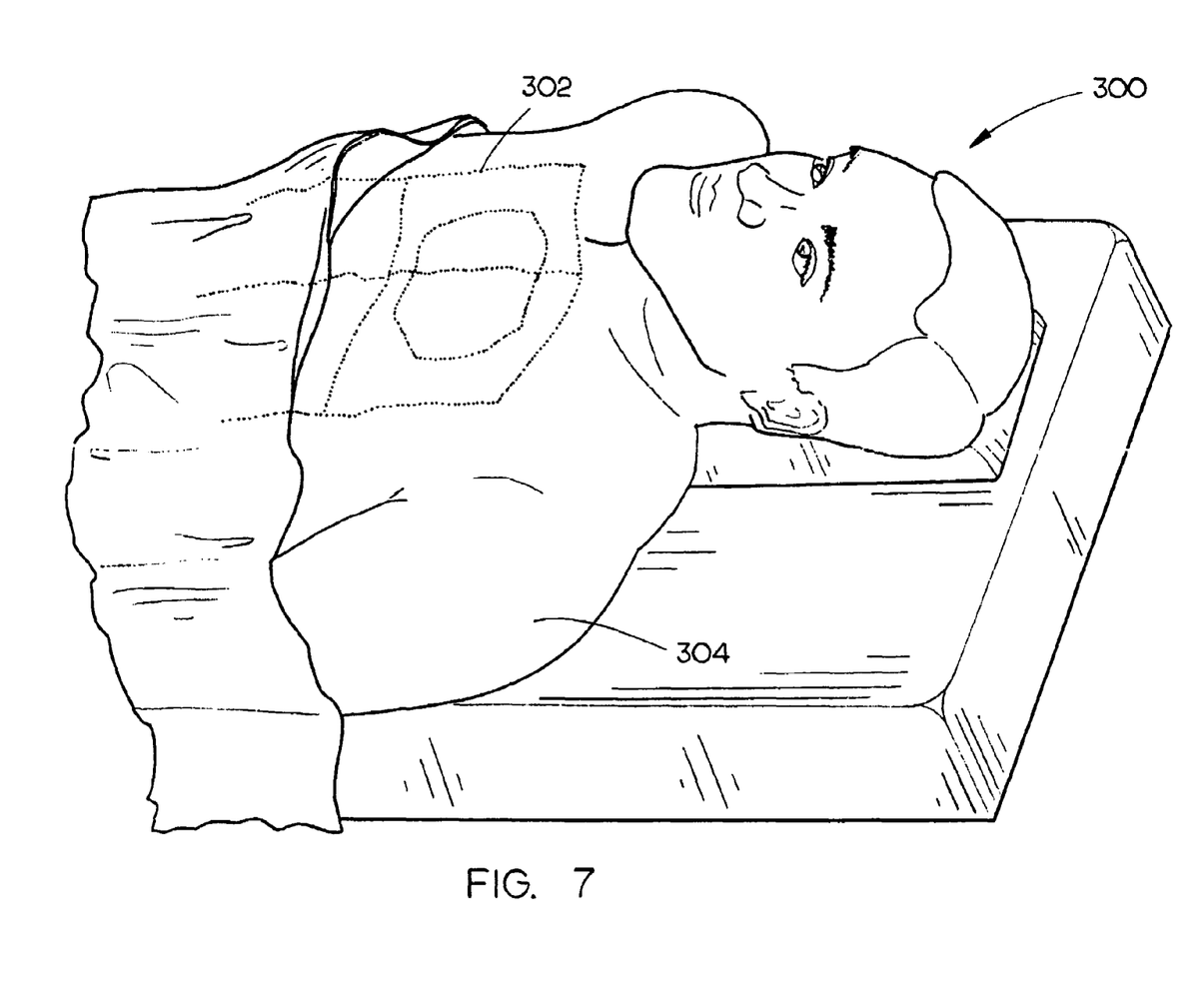

In one specific embodiment, the system 100 and method 200 illustrated in FIGS. 1 through 5 may be used in a radiation treatment device during patient set up. Accordingly, FIGS. 6 and 7 illustrate radiation treatment devices 300 employing the present invention for projecting a shape or pattern 302 onto a scene comprising the body 304 of a patient undergoing radiation treatment in accordance with exemplary embodiments of the present invention. In accordance with the present invention, the shape 302 is projected in such a manner that the shape appears to be projected via a light beam emanating from the radiation source of the radiation treatment device 300. However, it will be appreciated that the system 100 and method 200 described in the discussion of FIGS. 1, 2, 3, 4 and 5, are not limited to application in radiation treatment devices 300 as shown in FIGS. 6 and 7. Instead, it is contemplated that the system 100 and method 200 may be used in virtually any application where it is desirable to project a shape onto a scene so that the shape appears to emanate from a desired source location. Such applications may include medical diagnostic and/or treatment applications, manufacturing applications, object inspection applications, and the like.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A system for projecting a shape onto a scene so that the shape appears to emanate from a source location, comprising:
    a first projection assembly for projecting a first plane of light so that the first plane of light intersects the scene to form a first light stripe on the scene; and
    a second projection assembly for projecting a second plane of light so that the second plane of light intersects the scene to form a second light stripe on the scene, the first light stripe intersecting the second light stripe for defining a point of light projected onto the scene so that the point of light appears to emanate from the source location;
    wherein the first projection assembly rotates about a first axis extending through the source location and the second projection assembly rotates about a second axis extending through the source location for controlling the position of the point of light on the scene.

2. The system as claimed in claim 1, wherein the first projection assembly comprises a first mirror and the second projection assembly comprises a second mirror, the first mirror rotating about the first axis for reflecting the first plane of light so that the first plane of light is projected onto the scene and the second mirror rotating about the second axis for reflecting the second plane of light so that the second plane of light is projected onto the scene.

3. The system as claimed in claim 2, further comprising a first light source for projecting the first plane of light onto the first mirror for reflection by the first mirror and a second light source for projecting the second plane of light onto the second mirror for reflection by the second mirror.

4. The system as claimed in claim 1, wherein the first projection assembly comprises a first light source and the second projection assembly comprises a second light source, the first light source rotating about the first axis for projecting the first plane of light onto the scene and the second light source rotating about the second axis for projecting the second plane of light onto the scene.

5. The system as claimed in claim 1, further comprising an actuator assembly for rotating the first projection assembly and the second projection assembly.

6. The system as claimed in claim 5, further comprising a controller assembly for controlling rotation of the first projection assembly and the second projection assembly.

7. The system as claimed in claim 6, wherein the actuator assembly comprises a first actuator for rotating the first projection assembly and a second actuator for rotating the second projection assembly and the controller assembly comprises a first controller for controlling the first actuator and a second controller for controlling the second actuator.

8. The system as claimed in claim 7, wherein the first actuator and the second actuator comprise a galvanometer.

9. The system as claimed in claim 1, further comprising a computer for generating a first angle of rotation for the first projection assembly and a second angle of rotation for the second projection assembly from the position of a point in the shape to be projected into the scene.

10. The system as claimed in claim 9, wherein the computer generates the first angle of rotation and the second angle of rotation from:

$$\theta_1 = \sin^{-1}(|\hat{N}_1 \times \hat{N}_1'|)$$

and $$\theta_2 = \sin^{-1}(|\hat{N}_2 \times \hat{N}_2'|);$$

where $\theta_1$ is an angle of rotation by which a plane $P_1$ rotates about a rotation axis $SL_1$ in order to illuminate a point $\overline{p}$, $\theta_2$ is an angle of rotation by which a plane $P_2$ rotates about a rotation axis $SL_2$ in order to illuminate a point $\overline{p}$, $\hat{N}_1$ is a unit normal to the plane $P_1$, $\hat{N}_1$ being calculated from:

$$\hat{N}_1 = \frac{\overline{L_1} \times \overline{S}}{|\overline{L_1}||\overline{S}|};$$

$\hat{N}_1$' is a unit normal to the plane $P_1$', $\hat{N}_1$' being calculated from:

$$\hat{N}'_1 = \frac{(\overline{L_1} - \overline{p}) \times (\overline{S} - \overline{p})}{|\overline{L_1} - \overline{p}||\overline{S} - \overline{p}|};$$

$\hat{N}_2$ is a unit normal to the plane $P_2$, $\hat{N}_2$ being calculated from:

$$\hat{N}_2 = \frac{\overline{L_2} \times \overline{S}}{|\overline{L_2}||\overline{S}|}; \text{ and}$$

$\hat{N}_2$' is a unit normal to the plane $P_2$', $\hat{N}_2$' being calculated from:

$$\hat{N}'_2 = \frac{(\overline{L_2} - \overline{p}) \times (\overline{S} - \overline{p})}{|\overline{L_2} - \overline{p}||\overline{S} - \overline{p}|}.$$

11. A method for projecting a shape onto a scene so that the shape appears to emanate from a source location, comprising:
projecting a first plane of light from a first projection assembly so that the first plane of light intersects the scene to form a first light stripe on the scene;
projecting a second plane of light from a second projection assembly so that the second plane of light intersects the scene to form a second light stripe on the scene, the first light stripe intersecting the second light stripe for defining a point of light projected onto the scene so that the point of light appears to emanate from the source location; and
rotating at least one of the first projection assembly about a first axis extending through the source location and the second projection assembly about a second axis extending through the source location for controlling the position of the point of light on the scene.

12. The method as claimed in claim 11, wherein the first projection assembly comprises a first mirror and the second projection assembly comprises a second mirror, projecting the first plane of light comprises rotating the first mirror about the first axis for reflecting the first plane of light so that the first plane of light is projected onto the scene and projecting the second plane of light comprises rotating the second mirror about the second axis for reflecting the second pane of light so that the second plane of light is projected onto the scene.

13. The method as claimed in claim 12, further comprising illuminating a first light source for projecting the first plane of light onto the first mirror for reflection by the first mirror and illuminating a second light source for projecting the second plane of light onto the second mirror for reflection by the second mirror.

14. The method as claimed in claim 11, wherein the first projection assembly comprises a first light source and the second projection assembly comprises a second light source, projecting the first plane of light comprises rotating the first light source about the first axis for projecting the first plane of light onto the scene and projecting the second plane of light comprises rotating the second light source about the second axis for projecting the second plane of light onto the scene.

15. The method as claimed in claim 11, further comprising generating a first angle of rotation for the first projection assembly and a second angle of rotation for the second projection assembly from the position of a point in the shape to be projected into the scene.

16. The method as claimed in claim 11, wherein the the first angle of rotation and the second angle of rotation are determined from:

$$\theta_1 = \text{Sin}^{-1}(|\hat{N}_1 \times \hat{N}_1'|)$$

and $$\theta_2 = \text{Sin}^{-1}(|\hat{N}_2 \times \hat{N}_2'|);$$

where $\theta_1$ is an angle of rotation by which a plane $P_1$ rotates about a rotation axis $SL_1$ in order to illuminate a point $\overline{p}$, $\theta_2$ is an angle of rotation by which a plane $P_2$ rotates about a rotation axis $SL_2$ in order to illuminate a point $\overline{p}$, $\hat{N}_1$ is a unit normal to the plane $P_1$, $\hat{N}_1$ being calculated from:

$$\hat{N}_1 = \frac{\overline{L_1} \times \overline{S}}{|\overline{L_1}||\overline{S}|};$$

$\hat{N}_1$' is a unit normal to the plane $P_1$', $\hat{N}_1$' being calculated from:

$$\hat{N}'_1 = \frac{(\overline{L_1} - \overline{p}) \times (\overline{S} - \overline{p})}{|\overline{L_1} - \overline{p}||\overline{S} - \overline{p}|};$$

$\hat{N}_2$ is a unit normal to the plane $P_2$, $\hat{N}_2$ being calculated from:

$$\hat{N}_2 = \frac{\overline{L_2} \times \overline{S}}{|\overline{L_2}||\overline{S}|}; \text{ and}$$

$\hat{N}_2$' is a unit normal to the plane $P_2$', $\hat{N}_2$' being calculated from:

$$\hat{N}'_2 = \frac{(\overline{L_2} - \overline{p}) \times (\overline{S} - \overline{p})}{|\overline{L_2} - \overline{p}||\overline{S} - \overline{p}|}.$$

17. A system for projecting a shape onto a scene so that the shape appears to emanate from a source location, comprising:
means for projecting a first plane of light so that the first plane of light intersects the scene to form a first light stripe on the scene; and
means for projecting a second plane of light so that the second plane of light intersects the scene to form a second light stripe on the scene, the first light stripe intersecting the second light stripe for defining a point of light projected onto the scene so that the point of light appears to emanate from the source location;
wherein the first projecting means rotates about a first axis extending through the source location and the second projecting means rotates about a second axis extending through the source location for controlling the position of the point of light on the scene.

18. The system as claimed in claim 17, further comprising means for rotating the first projecting means and the second projecting means.

19. The system as claimed in claim 18, further comprising means for controlling rotation of the first projecting means and the second projecting means.

20. The system as claimed in claim 17, further comprising means for generating a first angle of rotation for the first projecting means and a second angle of rotation for the second projecting means from the position of a point in the shape to be projected into the scene.

21. The system as claimed in claim 20, wherein the generating means generates the first angle of rotation and the second angle of rotation from:

$$\theta_1 = \sin^{-1}(|\hat{N}_1 \times \hat{N}_1'|)$$

and $$\theta_2 = \sin^{-1}(|\hat{N}_2 \times \hat{N}_2'|);$$

where $\theta_1$ is an angle of rotation by which a plane $P_1$ rotates about a rotation axis $SL_1$ in order to illuminate a point $\bar{p}$, $\theta_2$ is an angle of rotation by which a plane $P_2$ rotates about a rotation axis $SL_2$ in order to illuminate a point $\bar{p}$, $\hat{N}_1$ is a unit normal to the plane $P_1$, $\hat{N}_1$ being calculated from:

$$\hat{N}_1 = \frac{\bar{L}_1 \times \bar{S}}{|\bar{L}_1||\bar{S}|};$$

$\hat{N}_1'$ is a unit normal to the plane $P_1'$, $\hat{N}_1'$ being calculated from:

$$\hat{N}_1' = \frac{(\bar{L}_1 - \bar{p}) \times (\bar{S} - \bar{p})}{|\bar{L}_1 - \bar{p}||\bar{S} - \bar{p}|};$$

$\hat{N}_2$ is a unit normal to the plane $P_2$, $\hat{N}_2$ being calculated from:

$$\hat{N}_2 = \frac{\bar{L}_2 \times \bar{S}}{|\bar{L}_2||\bar{S}|}; \text{ and}$$

$\hat{N}_2'$ is a unit normal to the plane $P_2'$, $\hat{N}_2'$ being calculated from:

$$\hat{N}_2' = \frac{(\bar{L}_2 - \bar{p}) \times (\bar{S} - \bar{p})}{|\bar{L}_2 - \bar{p}||\bar{S} - \bar{p}|}.$$

* * * * *